United States Patent [19]

Niwa

[11] Patent Number: 5,139,026
[45] Date of Patent: Aug. 18, 1992

[54] PULSE WAVE DETECTING APPARATUS AND PULSE WAVE DETECTING METHOD

[75] Inventor: Minoru Niwa, Nagoya, Japan

[73] Assignee: Colin Electronics Co., Ltd., Aichi, Japan

[21] Appl. No.: 548,889

[22] PCT Filed: Dec. 12, 1989

[86] PCT No.: PCT/JP89/01242
§ 371 Date: Jul. 24, 1990
§ 102(e) Date: Jul. 24, 1990

[87] PCT Pub. No.: WO90/06721
PCT Pub. Date: Jun. 28, 1990

[30] Foreign Application Priority Data

Dec. 12, 1988 [JP] Japan .................. 63-161128

[51] Int. Cl.$^5$ .............................. A61B 5/02
[52] U.S. Cl. ...................... 128/687; 128/672
[58] Field of Search ............ 128/672, 681, 687–690

[56] References Cited

U.S. PATENT DOCUMENTS

| | | | |
|---|---|---|---|
| 4,423,738 | 1/1984 | Newgard | 128/672 |
| 4,669,485 | 6/1987 | Russell | 128/679 |
| 4,699,152 | 10/1987 | Link | 128/681 |
| 4,799,491 | 1/1989 | Eckerle | 128/672 |
| 4,802,488 | 2/1989 | Eckerle | 128/672 |
| 4,836,213 | 6/1989 | Wenzel et al. | 128/672 |
| 4,893,631 | 1/1990 | Wenzel et al. | 128/672 |
| 4,924,871 | 5/1990 | Honeyager | 128/672 |
| 4,987,900 | 1/1991 | Eckerle et al. | 128/672 |
| 5,005,581 | 4/1991 | Honeyager | 128/681 |

FOREIGN PATENT DOCUMENTS

| | | |
|---|---|---|
| 0297146 | 7/1988 | European Pat. Off. . |
| 61-103432 | 5/1986 | Japan . |
| 61-247432 | 11/1986 | Japan . |
| 63-293424 | 1/1988 | Japan . |
| 63-77011 | 5/1988 | Japan . |
| 1214341 | 8/1989 | Japan . |
| 1232929 | 9/1989 | Japan . |
| 80/03387 | 5/1988 | World Int. Prop. O. . |
| 88/04910 | 7/1988 | World Int. Prop. O. .......... 128/687 |

Primary Examiner—William E. Kamm
Assistant Examiner—Kevin Pontius
Attorney, Agent, or Firm—Oliff & Berridge

[57] ABSTRACT

Pulse wave is detected by a pulse wave sensor pressed against an arterial vessel of living body. Stability of detection of the pulse wave may be insufficient due to not only inappropriate pressing of the pulse wave sensor but also the living body itself. The insufficient stability of detection of pulse wave resulting from the living body itself cannot be solved by altering the manner of pressing of the pulse wave sensor, but it can be solved by, for example, changing the angle of a hand about the wrist and thereby detecting a pulse wave produced from the radial artery running in the wrist. The present invention has made it possible to automatically identify the insufficient stability of detection of pulse wave due to the living body itself. According to the present invention, it is judged whether or not stability of detection of pulse wave is insufficient due to a living body itself, based upon a first pressing force range within which change of amplitudes of pulses of the pulse wave detected as the pressing force applied to the pulse wave sensor is changed, with respect to the pressing force, is smaller than a predetermined value, and a second pressing force within which change of minimum values of the pulses detected as the pressing force is changed, with respect to the pressing force, is smaller than a predetermined value, and an abnormality signal is generated which represents the insufficient stability of detection of pulse wave.

11 Claims, 4 Drawing Sheets

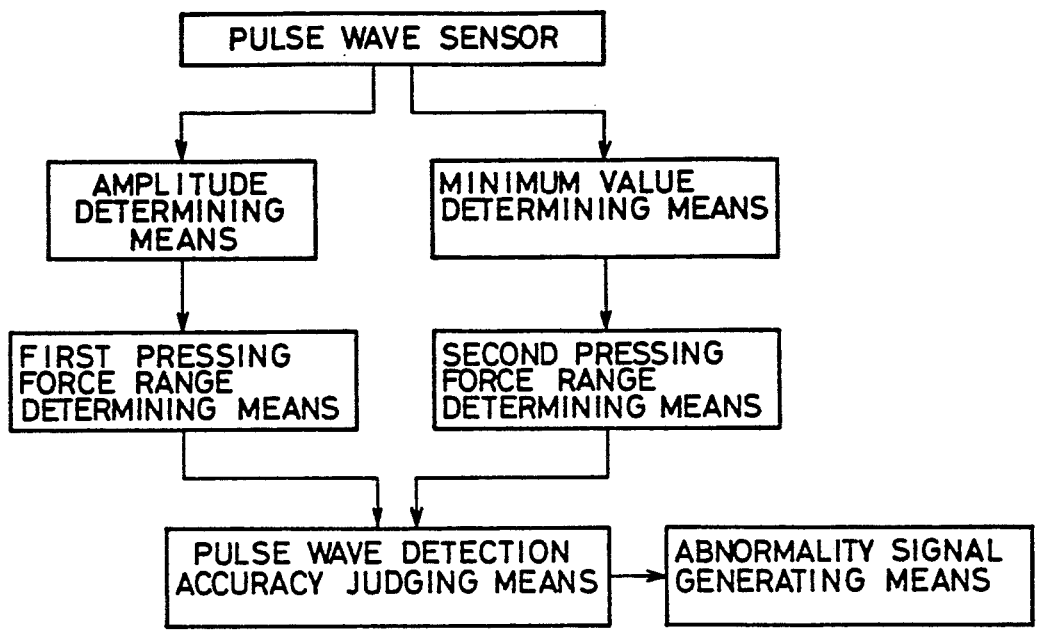
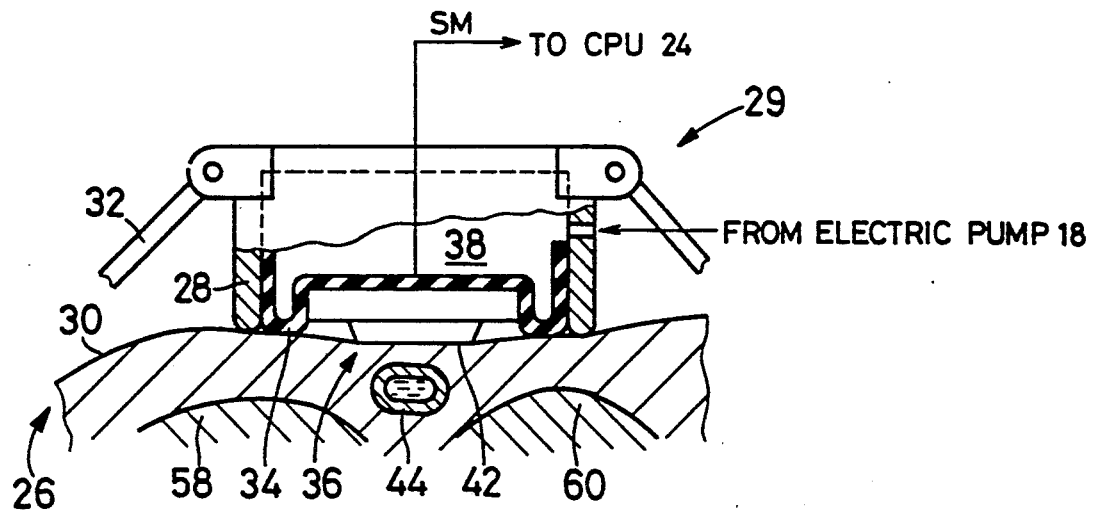

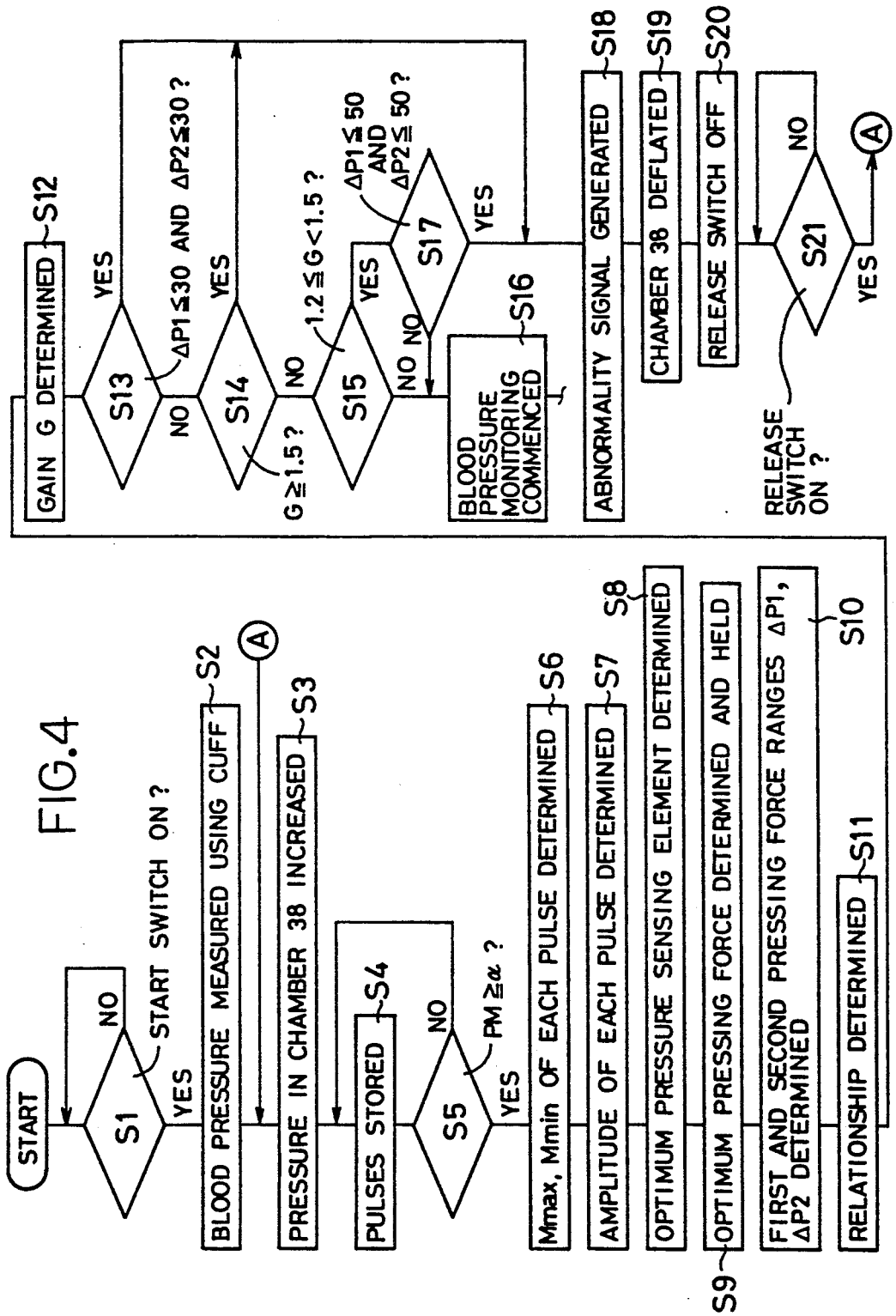

PULSE WAVE DETECTING APPARATUS AND PULSE WAVE DETECTING METHOD

FIELD OF THE INVENTION

The present invention relates to a pulse wave detecting apparatus.

BACKGROUND OF THE INVENTION

There is known a pulse wave detecting apparatus which detects a pulse wave using a pulse wave sensor which is pressed against an arterial vessel of a living body via a body surface with an optimum pressing force, the optimum pressing force being determined based upon a pulse wave detected by the pulse wave sensor while the pressing force applied to the pulse wave sensor is changed over a predetermined range.

In this pulse wave detecting apparatus, the pulse wave sensor is pressed against a wrist, for example. An optimum range of the pressing force applied to the pulse wave sensor within which a pulse wave having an appropriate magnitude is detected, is of considerably small width, in the case where the arterial vessel is positioned at a position nearer to the surface of the wrist than to the radius bone and tendon and for this reason the arterial vessel is flattened substantially before the pulse wave sensor is pressed toward the radius bone and tendon with a considerably great force, where the subject is so fat that the arterial vessel is positioned at a considerably deep position from the surface of the wrist, or where the arterial vessel is considerably thin. If this optimum pressing force range is considerably narrow, even a slight change in the pulse wave sensor pressing force, caused during the pulse wave detection, will lead to difficulty in detecting a pulse wave having an appropriate magnitude. This insufficient stability of detection of the pulse wave is due to the subject himself, not an error caused in the pulse wave detecting apparatus. For this reason, sufficient stability of detection of pulse wave cannot be obtained by re-activating the pulse wave detecting apparatus. In these cases, therefore, it is required to promptly identify that the stability of detection of pulse wave is insufficient due to the subject himself and take an appropriate measure on the subject, for example moving the hand inward about the wrist.

The present invention has been developed in the above-indicated situation. It is therefore an object of the present invention to provide a pulse wave detecting apparatus capable of identifying that stability of detection of pulse wave is insufficient due to a living body itself.

DISCLOSURE OF THE INVENTION

The above-indicated object has been achieved by the present invention, which provides a pulse wave detecting apparatus of the above-indicated type which, as shown in FIG. 1 corresponding to claims, is characterized by including (a) amplitude determining means for determining an amplitude of each of pulses of the pulse wave which are detected by the pulse wave sensor while the pressing force applied to the pulse wave sensor is changed, (b) first pressing force range determining means for determining a first pressing force range within which change of the amplitudes of the pulses determined by the amplitude determining means with respect to the pressing force is smaller than a predetermined value, (c) minimum value determining means for determining a minimum value of the each of pulses of the pulse wave which are detected by the pulse wave sensor while the pressing force is changed, (d) second pressing force range determining means for determining a second pressing force range within which change of the minimum values of the pulses determined by the minimum value determining means with respect to the pressing force is smaller than a predetermined value, (e) pulse wave detection stability judging means for judging whether or not stability of detection of pulse wave is insufficient due to the living body itself, based upon the first pressing force range determined by the first pressing force range determining means and the second pressing force range determined by the second pressing force range determining means, and (f) abnormality signal generating means for generating an abnormality signal representing that the stability of detection of pulse wave is insufficient, if the judgement of the pulse wave detection stability judging means is affirmative.

In the pulse wave detecting apparatus constructed as described above, the amplitude determining means determines an amplitude of each of pulses of the pulse wave which are detected by the pulse wave sensor while the pressing force applied to the pulse wave sensor is changed, and the first pressing force range determining means determines a first pressing force range within which change of the amplitudes of the pulses determined by the amplitude determining means with respect to the pressing force is smaller than a predetermined value. The minimum value determining means determines a minimum value of the each of pulses of the pulse wave which are detected by the pulse wave sensor while the pressing force is changed, and the second pressing force range determining means determines a second pressing force range within which change of the minimum values of the pulses determined by the minimum value determining means with respect to the pressing force is smaller than a predetermined value. The pulse wave detection stability judging means judges whether or not stability of detection of pulse wave is insufficient due to the living body itself, based upon the first and second pressing force ranges, and the abnormality signal generating means generates an abnormality signal representing that the stability of detection of pulse wave is insufficient, if the judgement of the pulse wave detection stability judging means is affirmative. Consequently, where the stability of detection of pulse wave is insufficient due to the living body itself, the abnormality signal generating means generates the abnormality signal. Thus, the insufficient stability of detection of pulse wave is promptly identified, and an appropriate measure can be taken on the living body for obtaining sufficient stability of detection of pulse wave.

The pulse wave detection stability judging means is preferably adapted to judge that the stability of detection of pulse wave is insufficient, if each of the first and second pressing force ranges has a width smaller than a first predetermined reference width.

It is preferred that the apparatus further include gain calculating means for calculating a gain that is a ratio of a difference between a systolic and a diastolic blood pressure of the living body measured using a cuff, to an amplitude of a pulse of the pulse wave detected by the pulse wave sensor, and that the pulse wave detection stability judging means be adapted to judge that the stability of detection of pulse wave is insufficient if the gain is greater than a first reference gain.

The pulse wave detection stability judging means is preferably adapted to judge that the stability of detection of pulse wave is insufficient, if the gain is not greater than the first reference gain and greater than a second reference gain smaller than the first reference gain, and if the width of the each of the first and second pressing force ranges is smaller than a second reference width greater than the first reference width.

It is preferred that the apparatus constitute a part of a blood pressure monitoring system having blood pressure measuring means for measuring using a cuff a blood pressure of the living body, the blood pressure monitoring system determining in advance a relationship between a blood pressure determined by the blood pressure measuring means and a magnitude of a pulse of the pulse wave detected by the pulse wave sensor, and continuously determining blood pressure values of the living body according to the determined relationship based upon pulses detected by the pulse wave sensor.

The pulse wave sensor may include a semiconductor chip having a press surface, and a plurality of pressure sensing elements provided on the press surface in a direction intersecting the arterial vessel. In this case, it is recommended that one of the plurality of pressure sensing elements which generates a pulse wave signal whose amplitude is the greatest be selected as an optimum pressure sensing element.

It is preferred that the apparatus further include pressing means for pressing the pulse wave sensor against the body surface of the living body, and means for determining as an optimum pressing force a pressing force at which a pulse wave signal generated by the optimum pressure sensing element exhibits a maximum amplitude as the pressing force of the pressing means is changed, and commanding the pressing means to hold the optimum pressing force.

According to the present invention, there is provided a pulse wave detecting method, preferably carried out by the invention apparatus, for detecting a pulse wave using a pulse wave sensor which is pressed against an arterial vessel of a living body via a body surface with an optimum pressing force, the optimum pressing force being determined based upon a pulse wave detected by the pulse wave sensor while the pressing force applied to the pulse wave sensor is changed over a predetermined range, the method being characterized by including the steps of (a) determining an amplitude of each of pulses of the pulse wave which are detected by the pulse wave sensor while the pressing force applied to the pulse wave sensor is changed, (b) determining a first pressing force range within which change of the amplitudes of the pulses determined in the amplitude determining step with respect to the pressing force is smaller than a predetermined value, (c) determining a minimum value of the each of pulses of the pulse wave which are detected by the pulse wave sensor while the pressing force is changed, (d) determining a second pressing force range within which change of the minimum values of the pulses determined in the minimum value determining step with respect to the pressing force is smaller than a predetermined value, (e) judging whether or not stability of detection of pulse wave is insufficient due to the living body itself, based upon the first pressing force range determined in the first pressing force range determining step and the second pressing force range determined in the second pressing force range determining step, and (f) generating an abnormality signal representing that the stability of detection of pulse wave is insufficient, if the judgement in the pulse wave detection stability judging step is affirmative.

The pulse wave detection accuracy judging step may include the step of judging that the stability of detection of pulse wave is insufficient, if each of the first and second pressing force ranges has a width smaller than a first reference width.

It is preferred that the method further include the step of calculating a gain that is a ratio of a difference between a systolic and a diastolic blood pressure of the living body measured using a cuff, to an amplitude of a pulse of the pulse wave detected by the pulse wave sensor, and that the pulse wave detection stability judging step include the step of judging that the stability of detection of pulse wave is insufficient if the gain is greater than a first reference gain.

The pulse wave detection accuracy judging step may include the step of judging that the stability of detection of pulse wave is insufficient, if the gain is not greater than the first reference gain and greater than a second reference gain smaller than the first reference gain, and if the width of the each of the first and second pressing force ranges is smaller than a second reference width greater than the first reference width.

BRIEF DESCRIPTION OF THE DRAWINGS

FIG. 1 is a view corresponding to claims of the present invention.

FIG. 3 is a view illustrating the pulse wave detector of the system of FIG. 2 secured to a wrist of a subject.

FIG. 4 is a flow chart according to which the blood pressure monitor system of FIG. 2 is operated.

BEST MODE FOR CARRYING OUT THE INVENTION

There will be described in detail an embodiment of the present invention by reference to the drawings.

Figure 2:
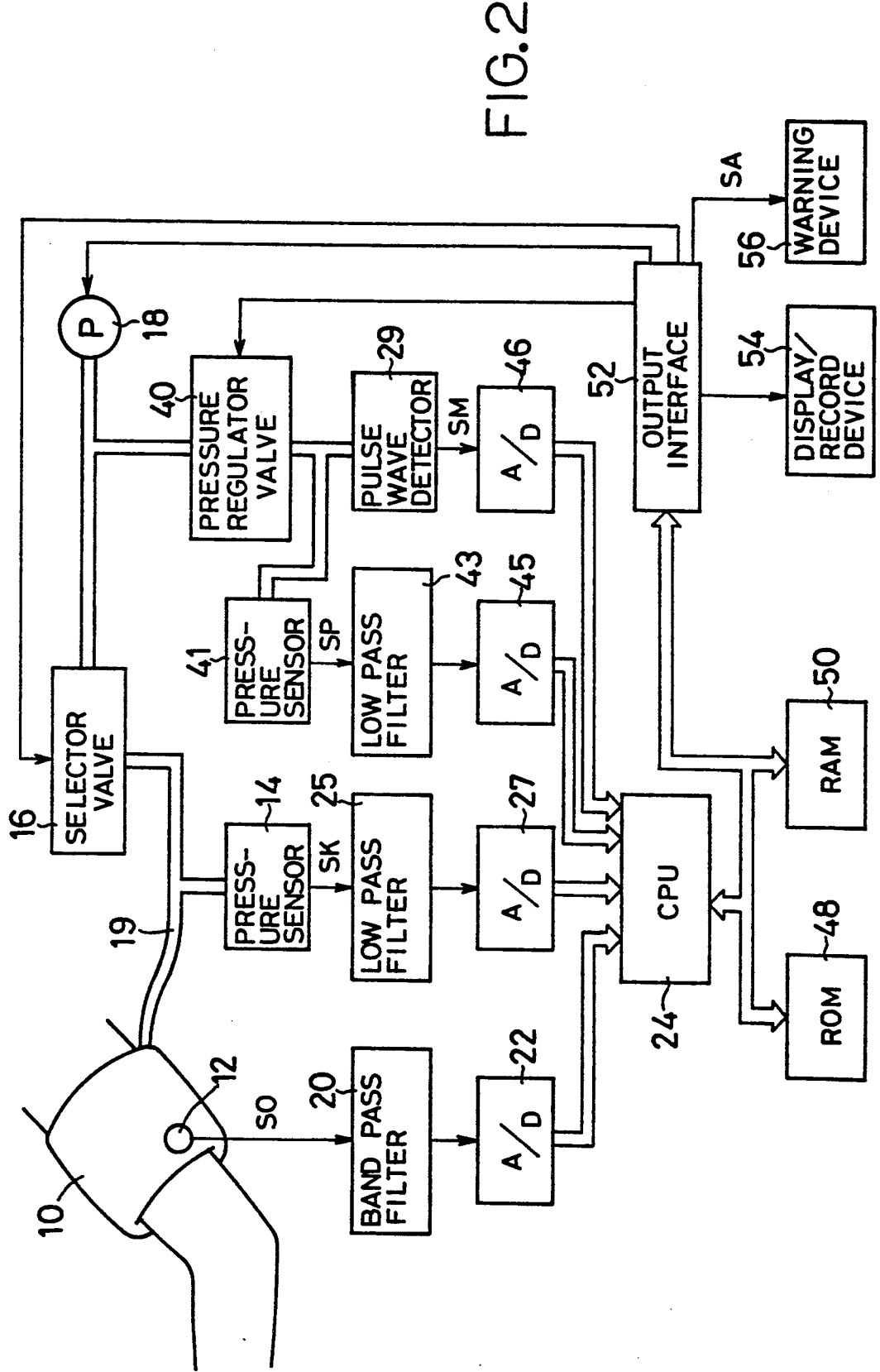
FIG. 2 is a view illustrating the arrangement of a blood pressure monitor system including a pulse wave detecting apparatus embodying the present invention.

FIG. 2 is a view illustrating the arrangement of a blood pressure monitor system including a pulse wave detecting apparatus embodying the present invention. In the figure, reference numeral 10 designates a rubber bag-like cuff which is wound around an upper arm or the like of a human being for pressing the upper arm. A microphone 12 is provided in the cuff 10. A pressure sensor 14, a selector valve 16, and an electric pump 18 are connected via piping 19 to the cuff 10. The electric pump 18 supplies the cuff 10 with a fluid such as air for increasing a pressure in the cuff 10. The microphone 12 detects pulse sounds (Korotkoff sounds) produced from an arterial vessel running in the upper arm of the living body, and supplies a band pass filter 20 with a pulse sound signal SO representative of the detected pulse sounds. The band pass filter 20 selectively transmits a signal component in the frequency range of, for example, 30 to 80 Hz. The pulse sound signal SO transmitted by the band pass filter 20 is supplied via an analog to digital converter 22 to a central processing unit 24. The pressure sensor 14 supplies a low pass filter 25 with a cuff pressure signal SK representative of the pressure in the cuff 10 (cuff pressure PK). The low pass filter 25 discriminates from cuff pressure signal SK a signal component representative of static pressure, and the discriminated cuff pressure signal SK is supplied via an A/D converter 27 to the CPU 24. The selector valve 16 is selectively placed in three positions thereof, that is, in the cuff inflation position in which the selector valve 16 permits fluid t be supplied to the cuff 10 for increasing cuff pressure PK, in the slow deflation position in which the selector valve 16 permits the cuff 10 to be slowly deflated, and in the rapid deflation position in which the selector valve 16 permits the cuff 10 is rapidly deflated.

Meanwhile, a pulse wave detector 29 is secured to a wrist 26, as shown in FIG. 3. The pulse wave detector 29 includes a cylindrical housing 28 having a bottom end and an open end. The housing 28 is detachably set on a body surface 30 with the help of a band 32, with the open end of the housing 28 being opposed to the body surface 30. A pulse wave sensor 36 is fixed to a diaphragm 34 within the housing 28, such that the pulse wave sensor 36 is movable relative to the housing 28 and advanceable from the open end of the housing 28. The housing 28 and the diaphragm 34 cooperate with each other to define a pressure chamber 38. The previously described electric pump 18 supplies the pressure chamber 22 with a pressurized fluid via a pressure regulator valve 40, so that the pulse wave sensor 35 is pressed against the body surface 30 with a pressing force corresponding to a pressure PM in the pressure chamber 38. A pressure sensor 41 is provided between the pressure regulator valve 40 and the pulse wave detector 29. The pulse wave sensor 41 supplies a low pass filter 43 a pressure signal SP representative of pressure PM in the pressure chamber 38. The low pass filter 43 discriminates from pressure signal SP a signal component representative of static pressure, and the discriminated pressure signal SP is supplied via an A/D converter 45 to the CPU 24.

The pulse wave sensor 36 is constituted by a semiconductor chip formed of, for example, monocrystalline silicon, and a multiplicity of pressure sensing elements (not shown), such as pressure sensing diodes, provided in a row on a press surface 42 of the semiconductor chip. The pulse wave sensor 36 is pressed against a radial artery 44 such that the row of the pressure sensing elements generally perpendicularly intersects the radial artery 44. In this situation, each pressure sensing element detects an oscillatory pressure wave, namely, pulse wave transmitted thereto from the radial artery 44 via the body surface 30. Each pressure sensing element converts the detected pulse wave to a pulse wave signal SM, and pulse wave signal SM is supplied via an A/D converter 46 to the CPU 24. In the present invention, the body surface 30 corresponds to a body surface of a living body, while the radial artery 44 corresponds to an arterial vessel of the living body.

The CPU 24 is coupled via data bus to a read only memory 48, a random access memory 50 and an output interface 52. The CPU 24 processes signals according to programs pre-stored in the ROM 48 by utilizing the temporary storage function of the RAM 50, and controls respective drive circuits (not shown) associated with the electric pump 18 and the selector valve 16 for regulating cuff pressure PK. As cuff pressure PK is slowly decreased in this way, an appearance and a disappearance of pulse sounds are detected and a systolic and a diastolic blood pressure are determined based on the detected pulse sounds. In addition, the CPU 24 controls a drive circuit (not shown) associated with the pressure regulator valve 40, for regulating pressure PM in the pressure chamber 38. As pressure PM is increased in this way, pulses of pulse wave are successively detected. These pulses are utilized for selecting from the plurality of pressure sensing elements of the pulse wave sensor 36 an optimum pressure sensing element, and determining an optimum pressing force with which the pulse wave sensor 36 is to be pressed against the radial artery 44. Further, the CPU 24 operates for continuously determining blood pressure values according to a relationship between blood pressure and pulse wave magnitude based on magnitudes of pulses of the pulse wave actually detected by the optimum pressure sensing element pressed with the optimum pressing force, and commands a display/record device 54 to display and record the determined blood pressure values. Meanwhile, the CPU 24 operates according to pre-stored programs for judging whether or not stability of detection of pulse wave is insufficient due to the subject himself, based on amplitudes and minimum values of the pulses which are detected by the optimum pressure sensing element as pressure PM is increased, and others. If this judgment is affirmative, the CPU 24 generates an abnormality signal SA to a warning device 56, which produces a warning that the stability of detection of pulse wave is insufficient. The warning device may be of the type producing a sound such as a buzzer or of the type producing a warning voice. In addition to, or in place of the warning produced by the warning device 56, the display/record device 54 may display an indication that the stability of detection of pulse wave is insufficient.

There will be described the operation of the blood pressure monitor system constructed as described above, by reference to the flow chart of FIG. 4.

Upon operation of a power switch (not shown), Step S1 is carried out in which it is judged whether or not a start switch (not shown) has been operated to an ON position thereof. If the judgement in Step S1 is affirmative, then Step S2 is carried out in which the upper arm is pressed by the cuff 10 and a blood pressure is measured as pressure PK in the cuff 10 is changed. This blood pressure measurement is of the Korotkoff sound type well known in the art. More specifically, first, the selector valve 16 is placed in the cuff inflation position and the electric pump 18 is activated to increase cuff pressure PK up to a pressure (e.g., 180 mmHg) higher than an estimated systolic blood pressure of the subject. Second, the selector valve 16 is switched from the cuff inflation position to the slow deflation position for slowly decreasing cuff pressure PK. Systolic and diastolic blood pressures are determined based on appearance and disappearance of the Korotkoff sounds which are detected in the form of pulse sound signal SO as cuff pressure PK is slowly decreased. A cuff pressure value PK when the Korotkoff sounds appear is determined as a systolic blood pressure H (mmHg), while a cuff pressure value PK when the Korotkoff sounds disappear is determined as a diastolic blood pressure L (mmHg). After the systolic and diastolic blood pressures H, L have been determined, the selector valve 16 is switched from the slow deflation position to the rapid deflation position for rapidly deflating the cuff 10. In this connection, it is noted that blood pressure values may be obtained as cuff pressure PK is increased.

After the cuff 10 has been deflated, Step S3 is carried out in which pressure PM in the pressure chamber 38 is comparatively slowly increased and thus pressing of the pulse wave sensor 36 against the body surface 30 is commenced. Step S3 is followed by Step S4 in which, as pressure PM is slowly increased in this way, pulse wave signals SM corresponding to one pulse of pulse wave are stored, together with pressure signal SP representative of pressure PM in the pressure chamber 38. Subsequently, Step S5 is carried out in which it is judged whether or not pressure PM has exceeded a reference pressure level $\alpha$ (e.g., 180 mmHg). If pressure PM has not reached pressure $\alpha$, Steps S4 and S5 are repeated so that pulses of pulse wave are stored in succession together with pressure PM with respect to each of pulse wave signals SM. On the other hand, if the judgement in Step S5 is affirmative, Step S6 is carried out in which are determined a maximum value Mmax (mV) and a minimum value Mmin (mV) of each of the pulses with respect to each of pulse wave signals SM stored in Step S4. In the present embodiment, Step S6 corresponds to minimum value determining means. Step S6 is followed by Step S7 in which an amplitude of each of the pulses is determined by calculating a difference between the maximum and minimum values Mmax, Mmin determined in Step S6. In the present embodiment, Step S7 corresponds to amplitude determining means. Subsequently, Step S9 is carried out in which a maximum amplitude is determined with respect to each of pulse wave signals SM, namely, each of the pressure sensing elements, and one of the pressure sensing elements whose maximum amplitude is the greatest of all the maximum amplitudes of the pressure sensing elements, is selected as an optimum pressure sensing element. Step S8 is followed by Step S9 in which a pressure PM when the greatest amplitude is detected by the optimum pressure sensing element is determined as an optimum pressure corresponding to an optimum pressing force with which the pulse wave sensor 36 is to be pressed against the radial artery 44. Then, pressure PM is adjusted to the determined optimum pressure and held thereat, and the electric pump 18 is deactivated.

Figure 5:
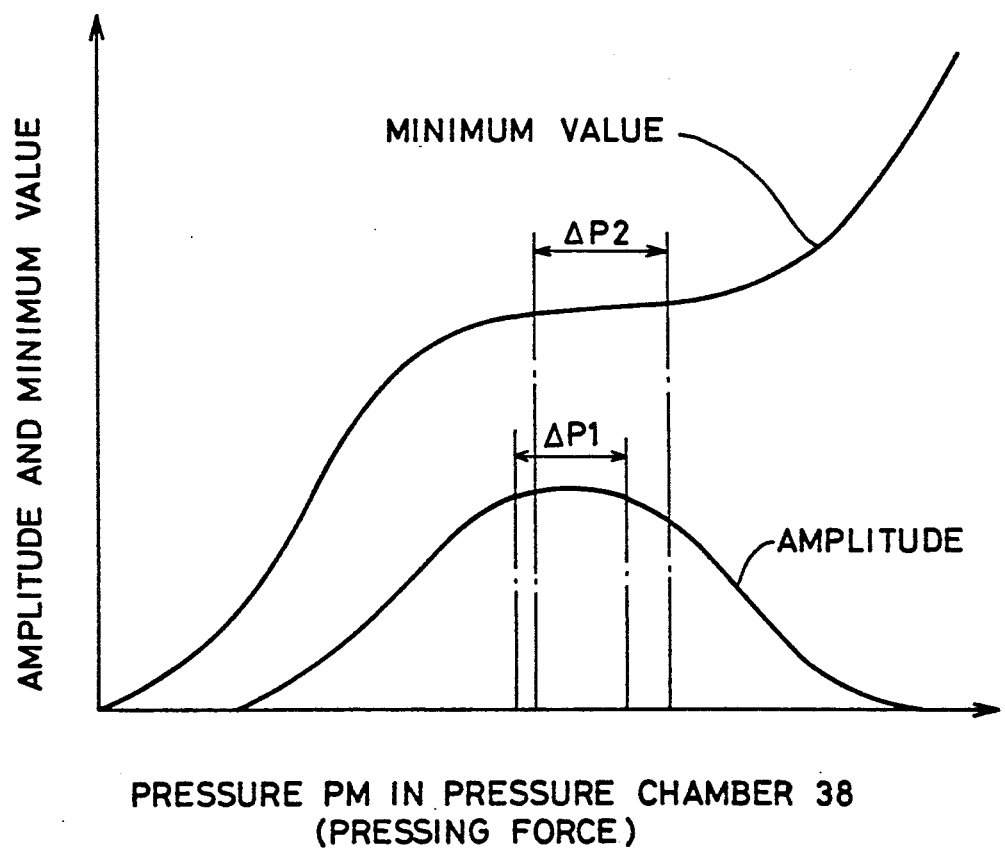
FIG. 5 is a graph showing curved lines representing a change of pulse amplitudes and a change of pulse minimum values each with respect to pressing force which changes are determined by carrying out the flow chart of FIG. 4.

Subsequently, Step S10 is carried out in which, as shown in FIG. 5, the amplitudes of the pulses detected by the optimum pressure sensing element and the corresponding pressure values PM (pressing forces applied to the pulse wave sensor 36) are utilized for determining a first pressing force range $\Delta$P1 within which change of the pulse amplitudes with respect to the pressing forces is smaller than a predetermined value (e.g., 7 mmHg). In addition, the minimum values of the pulses detected by the optimum pressure sensing element and the corresponding pressing forces applied to the pulse wave sensor 36 are utilized for determining a second pressing force range $\Delta$P2 within which change of the pulse minimum values with respect to the pressing forces is smaller than a predetermined value (e.g., 7 mmHg). In the present embodiment, Step S10 corresponds to first and second pressing force range determining means. In the graph of FIG. 5 the pulse amplitudes and the pulse minimum values are represented by curved lines, respectively, for easy understanding.

Step S10 is followed by Step S11 in which is determined a relational equation (1) defining a relationship between blood pressure $P_B$ and pulse magnitude M, according to which blood pressure values $P_B$, for example, a systolic blood pressure SYS and a diastolic blood pressure DIA are determined based on a maximum value Mmax and a minimum value Mmin, respectively, of each of pulses actually detected by the optimum pressure sensing element pressed with the optimum pressing force. For the determination of the relational equation (1), are used the following equations (2) and (3). Described in detail, the equation (2) is obtained by replacing parameters $P_B$ and M of the equation (1) with the actual systolic blood pressure H and the maximum value, Mmax', of the pulse corresponding to the optimum pressing force, respectively. Similarly, the equation (3) is obtained by replacing parameters $P_B$, M of the equation (1) with the actual diastolic blood pressure L and the minimum value, Mmin', of the same pulse, respectively. Unknown constants a and b are determined by the equations (2) and (3).

$$P_B = a \cdot M + b \tag{1}$$

$$H = a \cdot Mmax' + b \tag{2}$$

$$L = a \cdot Mmin' + b \tag{3}$$

Subsequently, Step S12 is carried out in which a gain G is determined according to the following equation (4):

$$G = (H - L)/A \tag{4}$$

where $A = Mmax' - Mmin'$

The gain G is a ratio of a maximum variation (H−L) of the pulse pressure measured using the cuff 10, to the amplitude A of the pulse detected by the optimum pressure sensing element pressed with the optimum pressing force.

Step S12 is followed by Step S13 in which it is judged whether or not each of the first and second pressing force ranges $\Delta$P1, $\Delta$P2 determined in Step S10 has a width not greater than a first reference width, for example 30 mmHg. If the judgement in Step S13 is negative, then Step S14 is carried out in which the gain G determined in Step S12 is not smaller than a first reference gain, for example 1.5. If the judgement in Step S14 is negative, that is, if the gain G is smaller than 1.5, then Step S15 is carried out in which it is judged whether the gain G is not smaller than a second reference gain, for example 1.2, namely it is judged whether or not the gain G satisfies the expression: $1.2 \leq G < 1.5$. If the judgement in Step S15 is negative, that is, if each of the first and second pressing force ranges $\Delta$P1, $\Delta$P2 is greater than 30 mmHg and the gain G is smaller than 1.2, that means that stability of detection of pulse wave is sufficient and that a pulse wave having an appropriate magnitude or amplitude is detected in a sufficiently stable manner. Step S15 is followed by Step S16 in which blood pressure monitoring is commenced. Described in more detail, a systolic and a diastolic blood pressure SYS and DIA are determined according to the relationship determined in Step S11 based on a maximum and a minimum value Mmax' and Mmin' of each of pulses successively detected by the optimum pressure sensing element pressed with the optimum pressing force. The determined systolic and diastolic blood pressure values SYS, DIA are displayed and recorded on and by the display/record device 54. Meanwhile, if the judgement in Step S15 is affirmative, then Step S17 is carried out in which it is judged whether or not the width of each of the first and second pressing force ranges $\Delta$P1, $\Delta$P2 is not greater than a second reference width, for example 50 mmHg. If the judgement in Step S17 is negative, then Step S16 is carried out in which blood pressure monitoring is commenced.

On the other hand, if the judgement in any of Steps S13, S14 and S17 is affirmative, that means that the stability of detection of pulse wave is insufficient due to the subject himself, and then Step S18 is carried out. For example, where the radial artery 44 is positioned, due to the angle of the hand with respect to the wrist 26, or other reasons, at a position nearer to the body surface 30 than to the radius bone 58 and tendon 60 and for this reason the radial artery 44 is deformed substantially flat before the pulse wave sensor 36 is pressed toward the radius bone 58 and tendon 60 with a considerably great pressing force, the judgement in Step S13, S14 or S17 is found affirmative. In addition, where the subject is so fat that the radial artery 44 is positioned at a considerably deep position from the body surface 30, and where the radial artery 44 is considerably thin, the affirmative judgement results in Step S13, S14 or S17. In these cases, an optimum range of the pressing force applied to the pulse wave sensor 36 in which range a pulse wave having an appropriate magnitude is detected, has only a considerably small width. For this reason, even a slight change in the pulse wave sensor pressing force, caused during the pulse wave detection, will lead to difficulty in detecting a pulse wave having an appropriate magnitude. In the present embodiment, Steps S13, S14, S15 and S17 correspond to pulse wave detection stability judging means.

In Step S18 an abnormality signal SA representing that the stability of detection of pulse wave is insufficient due to the subject himself, is generated to the warning device 56, which produces a warning. In the present embodiment Step S18 corresponds to abnormality signal generating means. Subsequently, Step S19 is carried out in which the pressure chamber 38 is deflated and then Step S20 is carried out in which a release switch (not shown) is placed in an OFF position thereof so that further operations are ceased on the system. Step S20 is followed by Step S21 in which it is judged whether or not the release switch has been operated to an ON position thereof so that the further operations are permitted. If the judgement in Step S21 is negative, Step S21 is repeated. During this repetition of Step S21, an appropriate measure is taken on the subject, such as moving the hand inward on the wrist 26. Meanwhile, if it is judged in Step S21 that the release switch has been placed in the ON position, then Step S3 and the following are carried out again.

As is apparent from the foregoing, in the present embodiment, the affirmative judgement in any of Steps S13, S14 and S17 means that the stability of detection of pulse wave is insufficient due to the subject himself, and in these events the warning device 56 produces a warning. From this warning the operator promptly notes that the stability of detection of pulse wave is insufficient due to the subject himself. Thus, the operator takes an appropriate measure on the subject for eliminating the problem and thereby avoiding pulse wave from being detected with insufficient stability due to the subject himself.

While in the illustrated embodiment Steps S13, S14, S15 and S17 correspond to the pulse wave detection stability judging means, the judging means may be otherwise constituted. For example, it is possible to omit Steps S14, S15 and S17 and use Step S13 only for judging the stability of detection of pulse wave.

In the illustrated embodiment, in the event that the warning device 56 has produced a warning, the operator needs to change the angle of the hand about the wrist 26 or take other appropriate measures. However, it is possible to automate the task. For example, an automatic adjusting device (not shown) is secured to the wrist 26, and after Step S19 the adjusting device is automatically actuated to adjust the angle of the hand about the wrist 26 and subsequently Steps S3 and the following are carried out.

In addition, although the present invention has been described in the blood pressure monitor system adapted to monitor blood pressure by utilizing pulse wave detected by the pulse wave detector 29, the present invention can find various applications different from the blood pressure monitoring.

In the illustrated embodiment, it is judged in Step S16, before commencement of the blood pressure monitoring, whether or not the stability of detection of pulse wave is insufficient due to the subject himself. However, it is possible to adapt the blood pressure monitor system to recurrently make the judgement also after the commencement of the blood pressure monitoring, in a manner similar to the illustrated embodiment or based on the gain G only. In this case, blood pressure measurements by use of the cuff 10 may be conducted at regular intervals of time, for updating the relationship determined in Step S11 and the gain G.

While in the illustrated embodiment the multiplicity of pressure sensing elements are provided on the press surface 42 of the pulse wave sensor 36, it is possible to replace them with a single pressure sensing element.

In addition, the pressure sensing elements employed in the illustrated embodiment may be constituted by various elements different from diodes or other semiconductor pressure sensing elements.

While the illustrated blood pressure monitor system is adapted to detect a pulse wave from the radial artery 44, the present invention provides advantages also in detecting a pulse wave from an arterial vessel different from the radial artery 44, such as a dorsal pedal artery.

It is to be understood that the present invention may be embodied with various modifications without departing from the scope of the invention.

I claim:

1. A pulse wave detecting apparatus for detecting a pulse wave from an arterial vessel of a living body via a body surface, the apparatus comprising:

pulse wave sensor means for detecting a pulse wave from said arterial vessel of said living body via said body surface;

pressing means for providing a pressing force for pressing said pulse wave sensor means against said arterial vessel via said body surface;

amplitude determining means for determining an amplitude of each of pulses of the pulse wave which are detected by said pulse wave sensor means while the pressing force applied to said pulse wave sensor means is changed;

first pressing force determining means for determining a first pressing force range within which change of the amplitudes of said pulses determined by said amplitude determining means with respect to said pressing force is smaller than a first predetermined value;

minimum value determining means for determining a minimum value of said each of pulses of the pulse wave which are detected by said pulse wave sensor means while said pressing force is changed;

second pressing force determining means for determining a second pressing force range within which change of the minimum values of said pulses determined by said minimum value determining means with respect to said pressing force is smaller than a second predetermined value;

pulse wave detection stability judging means for judging whether or not stability of detection of pulse wave is insufficient due to the living body itself, based upon the first pressing force range determined by said first pressing force range determining means and the second pressing force range determined by said second pressing force range determining means; and abnormality signal generating means for generating an abnormality signal representing that the stability of detection of pulse wave is insufficient, if the judgement of said pulse wave detection stability judging means is affirmative.

2. The apparatus as set forth in claim 1, wherein said pulse wave detection stability judging means judges that the stability of detection of pulse wave is insufficient, if each of said first and second pressing force ranges has a width smaller than a first reference width.

3. The apparatus as set forth in claim 1, further comprising:

blood pressure measuring means including a cuff, for measuring a systolic and a diastolic blood pressure of said living body; and gain calculating means for calculating a gain that is a ratio of a difference between said systolic and said diastolic blood pressure of the living body measured using said cuff, to an amplitude of a pulse of the pulse wave detected by said pulse wave sensor means, said pulse wave detection stability judging means judging that the stability of detection of pulse wave is insufficient if said gain is greater than a fist reference gain.

4. The apparatus as set forth in claim 3, wherein said pulse wave detection stability judging means judges that the stability of detection of pulse wave is insufficient, if said gain is not greater than a first reference gain and greater than a second reference gain smaller than said first reference gain, and if at least one of said first and second pressing force ranges has a width not smaller than a first reference width and the width of each of the first and second pressing force ranges is smaller than a second reference width greater than said first reference width.

5. The apparatus as set forth in claim 1, further comprising:

blood pressure measuring means including a cuff, for measuring a blood pressure of said living body;

mean for determining a relationship between a blood pressure determined by said blood pressure measuring means and a magnitude of a pulse of the pulse wave detected by said pulse wave sensor means; and means for continuously determining blood pressure values of said living body according to the determined relationship based upon magnitudes of pulses of the pulse wave detected by said pulse wave sensor means.

6. The apparatus as set forth in claim 1, wherein said pulse sensor means includes a semiconductor chip having a press surface, and a plurality of pressure sensing elements provided on said press surface in a direction intersecting said arterial vessel, the apparatus further comprising means for selecting one of said plurality of pressure sensing elements which generates a pulse wave signal whose amplitude is the greatest as an optimum pressure sensing element.

7. The apparatus as set forth in claim 6, further comprising means for determining as an optimum pressing force a pressing force at which a pulse wave signal generated by said optimum pressure sensing element exhibits a maximum amplitude as the pressing force of said pressing mean is changed, and commanding said pressing means to hold said optimum pressing force.

8. A pulse wave detecting method for detecting a pulse wave using a pulse wave sensor pressed against an arterial vessel of a living body via a body surface with an optimum pressing force, the optimum pressing force being determined based upon a pulse wave detected by the pulse wave sensor while the pressing force applied to the pulse wave sensor is changed over a predetermined range, the method comprising the steps of:

determining an amplitude of each of pulses of the pulse wave which are detected by said pulse wave sensor while the pressing force applied to said pulse wave sensor is changed;

determining a first pressing force range within which change of the amplitudes of said pulses determined in the amplitude determining step with respect to said pressing force is smaller than a predetermined value;

determining a minimum value of said each of pulses of the pulse wave which are detected by said pulse wave sensor while said pressing force is changed;

determining a second pressing force range within which change of the minimum values of said pulses determined in the minimum value determining step with respect to said pressing force is smaller than a predetermined value;

judging whether or not stability of detection of pulse wave is insufficient due to the living body itself, based upon the first pressing force range determined in the first pressing force range determining step and the second pressing force range determined in the second pressing force range determining step; and generating an abnormality signal representing that the stability of detection of pulse wave is insufficient, if the judgement in the pulse wave detection stability judging step is affirmative.

9. The method as set forth in claim 8, wherein the pulse wave detection stability judging step includes the step of judging that the stability of detection of pulse wave is insufficient, if each of said first and second pressing force ranges has a width smaller than a first reference width.

10. The method as set forth in claim 9, further including the step of calculating a gain that is a ratio of a difference between a systolic and a diastolic blood pressure of the living body measured using a cuff, to an amplitude of a pulse of the pulse wave detected by said pulse wave sensor, the pulse wave detection stability judging step including the step of judging that the stability of detection of pulse wave is insufficient if said gain is greater than a first reference gain.

11. The method as set forth in claim 10, wherein the pulse wave detection stability judging step includes the step of judging that the stability of detection of pulse wave is insufficient, if said gain is not greater than a first reference gain and greater than a second reference gain smaller than said first reference gain, and if at least one of said first and second pressing force ranges has a width not smaller than said first reference width and the width of said each of the first and second pressing force ranges is smaller than a second reference width greater than said first reference width.

* * * * *